United States Patent [19]

Pontremoli et al.

[11] Patent Number: 5,330,744
[45] Date of Patent: Jul. 19, 1994

[54] METHOD FOR INCREASING SENSITIVITY TO CHEMICALLY INDUCED TERMINAL DIFFERENTIATION

[75] Inventors: Sandro Pontremoli, Genoa, Italy; Ronald Breslow, Englewood, N.J.; Paul A. Marks, Bridgewater, Conn.; Richard A. Rifkind, New York, N.Y.

[73] Assignees: Sloan-Kettering Institute for Cancer Research; The Trustees of Columbia University in the City of New York, both of New York, N.Y.

[21] Appl. No.: 270,643

[22] Filed: Nov. 14, 1988

[51] Int. Cl.$^5$ .............. A61K 49/00; A61K 31/205; A61K 31/16

[52] U.S. Cl. ...................... 424/10; 514/556; 514/616

[58] Field of Search .............. 514/616, 556; 424/10

[56] References Cited

U.S. PATENT DOCUMENTS

| | | | |
|---|---|---|---|
| 4,882,346 | 11/1989 | Driscoll et al. | 514/389 |
| 4,935,450 | 6/1990 | Cone | 514/728 |
| 4,961,926 | 10/1990 | Gabrilove | 424/85.1 |
| 4,983,636 | 1/1991 | Takeuchi | 514/699 |

OTHER PUBLICATIONS

Chemical Abstracts: vol. 109(7) 47737e.

Primary Examiner—Frederick E. Waddell
Assistant Examiner—T. J. Criares
Attorney, Agent, or Firm—John P. White

[57] ABSTRACT

The present invention provides a method of selectively inducing terminal differentiation of neoplastic cells and thereby inhibiting proliferation of such cells which comprises treating the cells so as to render them resistant to an antitumor agent and contacting the resulting resistant cells under suitable conditions with an amount of a compound effective to selectively induce terminal differentiation of such cells. The compound has a structure:

$$[R-A]-B-[A_1-B_1-]_a[A_2-B_2-]_b[A_3-R_1].$$

The invention also concerns a method of treating a patient having a tumor characterized by proliferation of neoplastic which comprises administering to the patient an amount of an antitumor agent to render the cells resistant to the antitumor agent and subsequently administering to the patient an amount of the compound effective to selectively induce terminal differentiation of such neoplastic cells and thereby inhibit their proliferation.

18 Claims, 9 Drawing Sheets

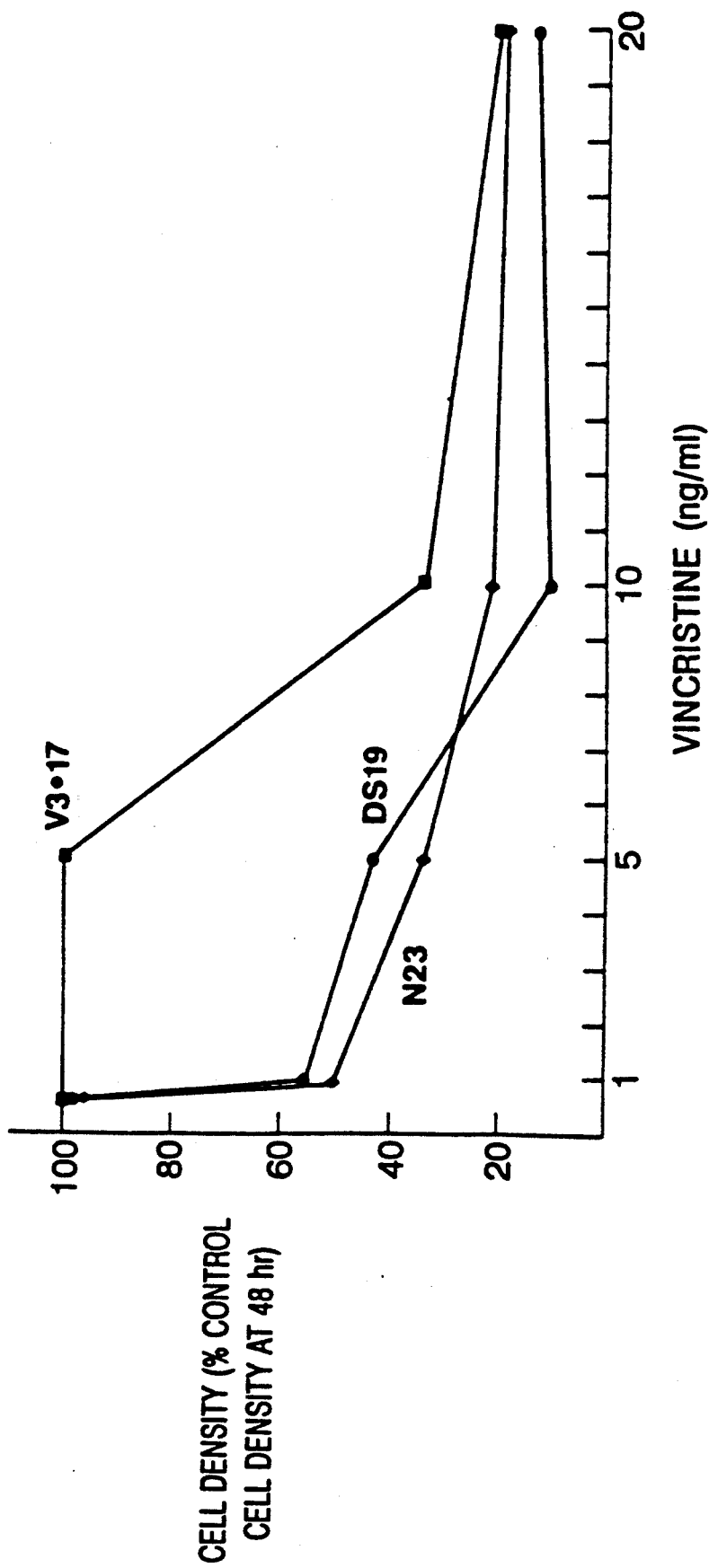

METHOD FOR INCREASING SENSITIVITY TO CHEMICALLY INDUCED TERMINAL DIFFERENTIATION

The invention described herein was made in the course of work under Grant Nos. CA-31768 and CA-08748 from the National Cancer Institute, U.S. Department of Health and Human Services. The U.S. Government has certain rights in this invention.

BACKGROUND OF THE INVENTION

Throughout this application various publications are referenced by arabic numerals within parentheses. Full citations for these publications may be found at the end of the specification immediately preceding the claims. The disclosures of these publications in their entireties are hereby incorporated by reference into this application in order to more fully describe the state of the art to which this invention pertains. Some of the information set forth herein has been published. See E. Melloni, S. Pontremoli, G. Damiani, P. Viotti, N. Welch, R. A. Rifkind, and P. A. Marks, Vincristine-Resistant Erythroleukemia Cell Line Has Marked Increased Sensitivity To Hexamethylenebisacetamide-Induced Differentiation, Proc. Natl. Acad. Sci USA, 85:3835-3839, June 1988.

Hexamethylene bisacetamide (HMBA)-mediated murine erythroleukemia (MEL) cell terminal differentiation is a multistep process (1,2). Upon culture of MEL cell line 745A-DS19 (DS19) (3) with HMBA (4) there is a latent period of approximately 10 to 12 hours during which commitment to terminal differentiation cannot be detected. Commitment is defined as the capacity to express characteristics of the erythroid differentiated phenotype, including loss of proliferative capacity, despite removal of the inducer (5,6). This early, latent period is followed by a period during which an increasing proportion of the population expresses characteristics of terminal differentiation, including loss of proliferative capacity.

During the latent period the inducer initiates a number of metabolic changes which precede irreversible commitment to differentiation. Among these are alterations in membrane permeability which involve sodium, potassium and calcium flux (7-9), changes in cell volume (10), a transient increase in cyclic AMP concentration (11), a prompt increase in membrane-associated protein kinase C activity (PKC), the appearance in the cytosol of a $Ca^{2+}$ and phospholipid-independent form of PKC, presumably generated by proteolytic cleavage of membrane-bound PKC (12), and the modulation in expression of a number of genes, including c-myb, c-myc, c-fos and p53 (13-16). Upon more prolonged culture with HMBA, DS19 cells become irreversibly committed (5,6). Morphological and molecular changes occur which are similar to normal erythroid terminal cell differentiation, including the coordinated expression of genes for $\alpha^1 \beta^{maj}$ globin, for the heme synthetic enzymes and for erythroid-specific membrane proteins, as well as suppression of DNA replication and rRNA synthesis (1,17,18).

The present invention involves the development of cell lines resistant to an antitumor agent, specifically a MEL cell line derived from DS19 which has been developed is resistant to inhibition of cell growth by vincristine and is designated V3.17. This MEL cell line, V3.17, is unexpectedly markedly more sensitive to HMBA-induced terminal erythroid differentiation.

Another striking characteristic of HMBA induced V3.17 commitment is the absence of the latent period characteristic of induced DS19 differentiation. In addition, the tumor promotor, phorbol-12-myristate-13-acetate (TPA) and the steroid, dexamethasone, both potent inhibitors of HMBA-mediated DS19 cell differentiation (2,19), fail to inhibit differentiation of V3.17 cells.

Moreover, the present invention provides a method for increasing the sensitivity of neoplastic cells to chemical inducers of terminal differentiation, such as HMBA, which involves rendering the cells resistant to an antitumor agent. This method may be used in the treatment of patients having tumors characterized by the proliferation of neoplastic cells.

SUMMARY OF THE INVENTION

The present invention provides a method of selectively inducing terminal differentiation of neoplastic cells and thereby inhibiting proliferation of such cells which comprises treating the cells so as to render them resistant to an antitumor agent and contacting the resulting resistant cells under suitable conditions with an amount of a compound effective to selectively induce terminal differentiation of such cells. The compound has a structure:

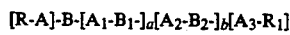

wherein each of A, $A_1$, $A_2$, and $A_3$ represent a polar group which comprises a nitrogen, sulfur or oxygen atom and wherein each of A, $A_1$, $A_2$, and $A_3$ may independently be the same as, or different from, the others of A, $A_1$, $A_2$, and $A_3$;

wherein each of R and $R_1$ is a hydrogen atom; a lower alkyl, alkenyl, or alkynyl group; or a group having the structure:

each $R_2$ and $R_3$ being a hydrogen atom or a lower alkyl, alkenyl, or alkynyl group; and wherein each of R, $R_1$, $R_2$ and $R_3$ may independently be the same as, or different from, the others of R, $R_1$, $R_2$, and $R_3$;

wherein each [R-A] and [$A_3$-$R_1$] have a dipolar moment greater than about 2.7 Debye units;

wherein each of B, $B_1$, and $B_2$ represents a nonpolar group which comprises at least 4 atoms in a chain, the termini of which chains are attached to A and $A_1$, $A_1$ and $A_2$, and $A_2$ and $A_3$ respectively; wherein each such atom is oxygen, nitrogen, carbon, or sulfur and wherein each of B, $B_1$, and $B_2$ may independently be the same as, or different from, the others of B, $B_1$, and $B_2$;

and wherein each of a and b is independently 0 or 1.

The invention also concerns a method of treating a patient having a tumor characterized by proliferation of neoplastic cells which comprises administering to the patient an amount of an antitumor agent to render the cells resistant to the antitumor agent and subsequently administering to the patient an amount of the compound effective to selectively induce terminal differentiation of such neoplastic cells, thereby inhibiting their proliferation and suppressing oncogenicity.

BRIEF DESCRIPTION OF THE FIGURES

FIG. 1: Effect of vincristine on MEL cell growth. MEL cell lines DS19 (●) and N23 (♦) were not selected for resistance to vincristine. V3.17 cell line (■) was selected for resistance to vincristine (see text for details). Cell density is expressed as a percent of the cell density of each cell line grown for 48 hrs in culture without vincristine.

FIG. 5A: cells grown without addition (♦) control), with HMBA (▲ HMPA), with dexamethasone (● DEXA), with TPA (▼ TP.\), with HMBA and dexamethasone (■ H+Dexa) and with HMBA and TPA (♦ H+TPA). FIG. 5B: V377 cells grown under similar conditions as indicated for DS19.

DETAILED DESCRIPTION OF THE INVENTION

Figure 2A:
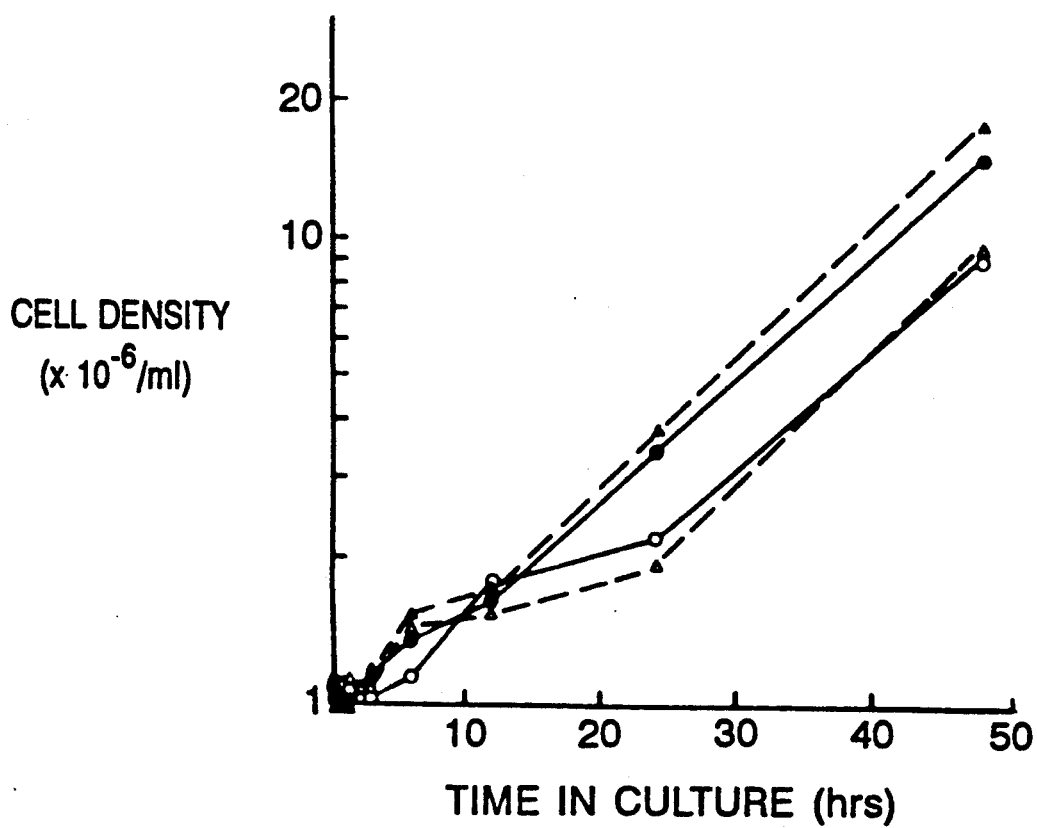
FIGS. 2A-2C: HMBA effect on cell growth (FIG. 2A), benzidine reactive cells (FIG. 2B), and commitment (FIG. 2C) of DS19 MEL cells grown without (●) or with HMBA (○) and V3.17 MEL cells grown without (▲) or with HMBA (△).

The present invention provides a method of selectively inducing terminal differentiation of neoplastic cells and thereby inhibiting proliferation of such cells which comprises treating the cells so as to render them resistant to an antitumor agent and contacting the resulting resistant cells under suitable conditions with an amount of a compound effective to selectively induce terminal differentiation of such cells. The compound has a structure:

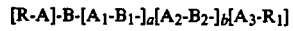

wherein each of A, $A_1$, $A_2$, and $A_3$ represent a polar group which comprises a nitrogen, sulfur or oxygen atom and wherein each of A, $A_1$, $A_2$, and $A_3$ may independently be the same as, or different from, the others of A, $A_1$, $A_2$, and $A_3$;

wherein each of R and $R_1$ is a hydrogen atom; a lower alkyl, alkenyl, or alkynyl group; or a group having the structure:

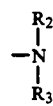

each $R_2$ and $R_3$ being a hydrogen atom or a lower alkyl, alkenyl, or alkynyl group; and wherein each of R, $R_1$, $R_2$ and $R_3$ may independently be the same as, or different from, the others of R, $R_1$, $R_2$, and $R_3$;

wherein each [R-A] and [$A_3$-$R_1$] have a dipolar moment greater than about 2.7 Debye units;

wherein each of B, $B_1$, and $B_2$ represents a nonpolar group which comprises at least 4 atoms in a chain, the termini of which chains are attached to A and $A_1$, $A_1$ and $A_2$, and $A_2$ and $A_3$ respectively; wherein each such atom is oxygen, nitrogen, carbon, or sulfur and wherein each of B, $B_1$, and $B_2$ may independently be the same as, or different from, the others of B, $B_1$, and $B_2$;

and wherein each of a and b is independently 0 or 1.

The antitumor agent may be one of numerous chemotherapy agents such as an alkylating agent, an antimetabolite, a hormonal agent, an antibiotic, colchicine, a vinca alkaloid, L-asparaginase, procarbazine, hydroxyurea, mitotane, nitrosoureas or an imidazole carboxamide. Suitable agents are those which promote depolarization of tubulin. Preferably the antitumor agent is colchicine or a vinca alkaloid; especially preferred are vinblastine and vincristine. In embodiments where the antitumor agent is vincristine, the cells preferably are treated so that they are resistant to vincristine at a concentration of about 5 ng/ml.

Compounds which are suitable for the practice of the present invention are made up of two components. One component comprises a polar group, i.e. functional groups with significant dipole moments, such as amides, sulfoxides, amine oxides and related functional groups.

The terminal portions of the compound, represented by R-A and $A_3$-$R_1$, each have dipole moments greater than about 2.7 debye units. The polar groups within the compound, represented by —$A_1$— and —$A_2$—, have significant dipolar moments but not necessarily in excess of 2.7 debye units. In the preferred embodiments, the polar groups are carbonyl radicals or bivalent radicals of an amide, a sulfoxide or a amine oxide. Each polar group need not necessarily be the same as the other polar groups. In the most preferred embodiments, the polar groups within the compound are the same as each other and the terminal polar groups are the same. Preferably, all the polar groups are amide groups attached to the compound at the nitrogen atom or at the carbon atom of the carbonyl radical. The amide group may comprise one or more hydrocarbon substituents, such as a lower alkyl or alkenyl groups, including branched or unbranched groups. The term "lower alkyl or alkenyl group" is intended to include saturated and unsaturated hydrocarbon groups with 1 to about 5 carbon atoms.

The embodiments where b is 0 (a is 1 or 0) and A is a carbonyl radical or a group having the structure:

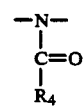

wherein $R_4$ is a hydrogen atom or a lower alkyl or alkenyl group, have proven to be the most useful embodiments to date.

Particularly preferred are compounds where b is 0 and A is a carbonyl radical and R has the structure:

wherein $R_2$ and $R_3$ each is hydrogen atom, a methyl group or a ethyl group.

The compound also requires at least one nonpolar section, designated B, which is attached to and connects polar groups. Additional nonpolar sections may also be present, e.g. $B_1$ when a is 1 and $B_2$ when b is 1. The nonpolar sections may comprise linear saturated hydrocarbon chains, linear unsaturated hydrocarbon chains containing one or more double or triple bonds, or saturated or unsaturated hydrocarbon chains containing one or more lower alkyl or alkenyl groups or small carbocyclic rings as substituents. In one of the preferred embodiments, the nonpolar groups are hydrocarbon chains comprising 4 to 7 methylene groups, especially preferred are hydrocarbon chains containing 6 carbon atoms.

The most preferred compounds for the practice of the present invention are those having the structures:

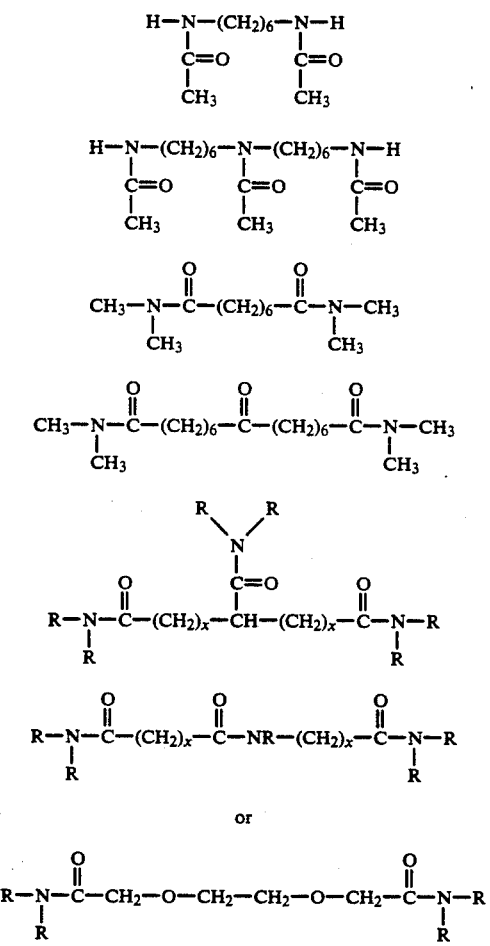

wherein R is hydrogen or a methyl group and x is 5 or 6.

The amount of the compound useful for the practice of the described method is in the range from about 0.1 mM to about 15 mM, preferably from about 0.5 mM to about 3 mM. Additionally, the treating of the cells with the antitumor agent may be effected by contacting the cells with the agent for a period of at least 3-5 days. The contacting of the resulting cells with the compound should be continuous for at least 36 hours.

The invention also concerns a method of treating a patient having a tumor characterized by proliferation of neoplastic cells which comprises administering to the patient an amount of an antitumor agent to render the cells resistant to the antitumor agent and subsequently administering to the patient an amount of the compound effective to selectively induce terminal differentiation of such neoplastic cells, thereby inhibiting their proliferation and suppressing oncogenicity.

The method of the present invention is intended for the treatment of human patients with tumors. However, it is also likely that the method would be effective in the treatment of tumors in other animals. The term tumor is intended to include any cancer caused by the proliferation of neoplastic cells, such as lung cancer, acute lymphoid myeloma, bladder melanoma, renal carcinoma, breast carcinoma, or colorectal carcinoma. The administration of the compound to the patient may be effected orally or parenterally. To date, administration intravenously has proven to be effective. The administration of the compound must be preformed continuously for a prolonged period of time, such as for at least 3 days, preferably more than 5 days. In the most preferred embodiments, the administration is effected continuously for at least 10 days and is repeated at intervals wherein at each interval the administration is continuously effected for at least 10 days. For example, the administration may be effected at intervals of 5-35 days, preferably about 25 days, and continuously for at least 10 days during each such interval.

The amount of the compound administered to the patient is less than an amount which would cause toxicity in the patient. In the preferred embodiments wherein the compound has the structure:

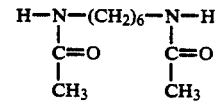

the amounts of the compound which is administered to the patient is less than the amount which causes a concentration of the compound in the patient's plasma to equal or exceed about 1.5 mM. Preferably, the concentration of the compound in the patient's plasma is maintained at about 1.0 mM. It has been found that administration of the above compound in an amount from about 5 gm/m²/day to about 30 gm/m²/day, particularly 20 gm/m²/day, is effective for the practice of the invention without producing toxicity in the patient. The optimal amount of the compound to be administered to the subject will depend on the particular compound. The amount may vary from about 0.5 to about 60 gm/m²/day.

The invention is illustrated in the Experimental Detail and Experimental Discussion sections which follow. These sections are set forth to aid in an understanding of the invention but are not intended to, and should not be construed to, limit in any way the invention as set forth in the claims which follow thereafter.

EXPERIMENTAL DETAILS

Materials and Methods

Cell Culture and Materials

MEL cell line DS19, and cell lines derived from it, namely N23 and V3.17, were maintained in alpha MEM medium containing 10% (v/v) fetal calf serum (2). MEL cell line N23 is a sub-clone of DS19 (20) and, just as DS19, was used in these studies to compare with the vincristine-resistant MEL cell line, V3.17, which was derived as described below. Cultures were initiated with an innoculum of $10^5$ cells/ml in Corning 75 cm$^2$ flasks; HMBA (4) was added to cultures at a final concentration of $5 \times 10^{-3}$M unless otherwise indicated below.

$^{32}$P-ATP was obtained from Amersham. DEAE cellulose (type DE 52) was purchased from Whatman. Dexamethasone, phosphatidylserine, 1,2-diolein, histone (type III-S), leupeptin, vincristine sulfate and TPA were purchased from Sigma.

Cell density, benzidine-reactive cells and hemoglobin content were assayed as detailed elsewhere (2,12).

Isolation of a MEL Cell Line Resistant to Vincristine

A MEL cell line resistant to vincristine was derived from cell line DS19 as follows: cells were cultured with 500 mg/ml vincristine for 3 days, then dead cells were separated from viable cells by density gradient centrifugation on lymphocyte separation medium (Flow no. 16-920-54) for 20 min at 1000x g at room temperature. Cells at the interface were recovered, washed 1x in culture medium and resuspended at $10^5$ cells/ml in medium containing 200 ng/ml vincristine and cultured for 4 days. Surviving cells were recovered by centrifugation, resuspended in fresh medium without vincristine and cultured for 22 days. Cells were again recovered by centrifugation, and resuspended in culture medium and passaged at 2 day intervals in culture with vincristine (5 ng/ml), maintained continuously in this manner and were designated V3.17.

Commitment Assay

Commitment, characterized by the irreversible induction of differentiation and limited cell division (small colony size), was assayed as previously described (6). MEL cells were transferred from suspension culture with inducer to semi-solid medium (1.8% methyl cellulose) without inducer and, after 5 days, the plates were stained for hemoglobin and scored for colony size (6).

RNA Preparation

Total RNA was prepared by the guanidinium isothiocyanate method and polyadenylated (poly A+) RNA isolated by oligo (dt)-cellulose chromatography (21,22).

Globin mRNA Assay

The $\alpha^1$, $\beta^{maj}$, and $\beta^{min}$ globin RNA probes used in these studies were previously described (23). RNase protection assays were carried out as described by Melton (24). Globin probes were hybridized with 10 $\mu$g of total cellular RNA. Protected RNA fragments were analyzed by electrophoresis on 8% polyacrylamide-8M urea denaturing gels. Relative quantitation was by liquid scintillation of individual gel bands.

Protein Kinase C Activity

PKC activity was assayed as previously described (4).

RESULTS

Growth of MEL Cell Lines with Vincristine

MEL cell lines DS19, N23 and V3.17 were grown in culture without vincristine and with increasing amounts of vincristine between 0.5 and 20 ng/ml. The vincristine-sensitive cell lines, DS19 and N23, showed marked growth inhibition at vincristine concentrations of 1.0 ng/ml or higher, while V3.17 cells, selected for their vincristine resistance, grew in concentrations up to 5 ng/ml, at rates similar to cells in the absence of vincristine (FIG. 1). The rate of increase in cell density of V3.17 cells grown in culture with 5 ng/ml vincristine was similar to that of DS19 cells and N23 cells grown without vincristine (FIG. 2A).

Figure 2B:
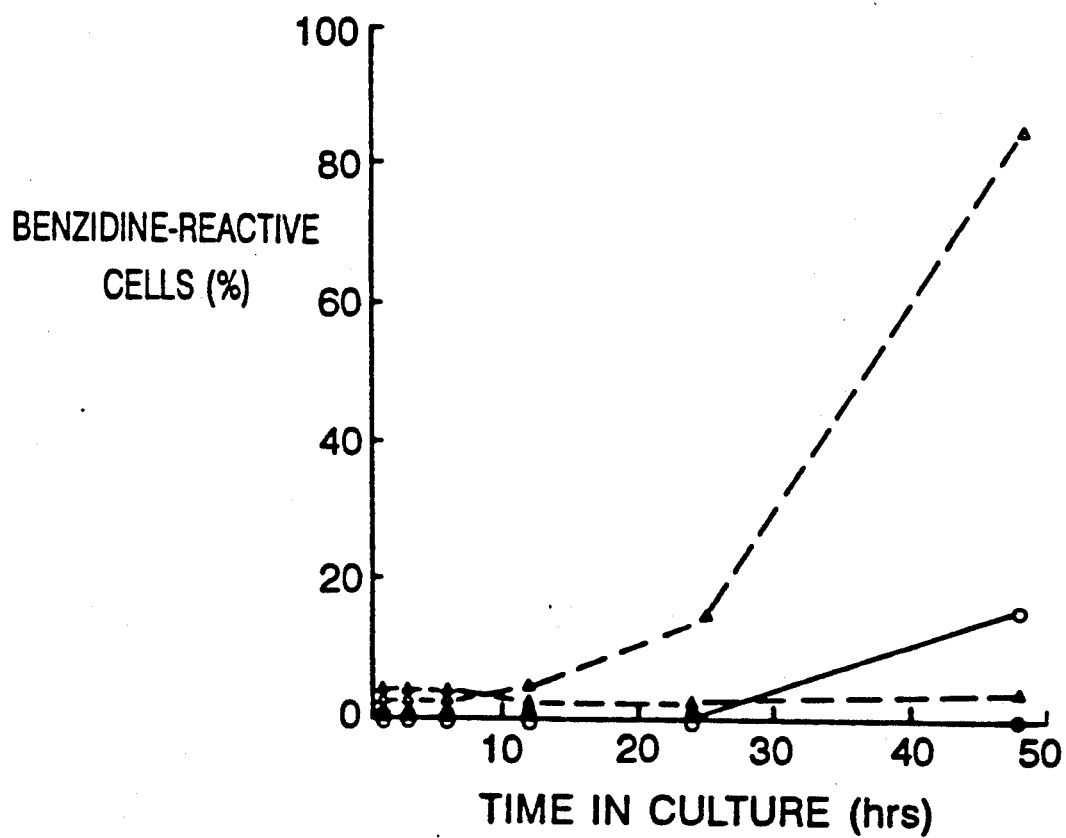

Effect of HMBA on V3.17 MEL Cell Growth, Commitment and Development of Benzidine-Reactive Cells HMBA decreased the cell density of V3.17 cells by about 50% at 48 hrs., which was similar to the decrease in cell density of DS19 in the presence of inducer (FIG. 2A). The V3.17 cell line displayed distinctly more (3-4%) spontaneously differentiating cells (benzidine-reactive without exposure to HMBA) than DS19 cells (<1.0%). After 24 hrs exposure to HMBA, V3.17 cells are 15% benzidine-reactive while there were less than 1% benzidine-reactive DS19 cells. By 48 hrs, when DS19 cells are about 15% benzidine-reactive, 85% of V3.17 cells contain stainable hemoglobin (FIG. 2B).

Figure 2C:
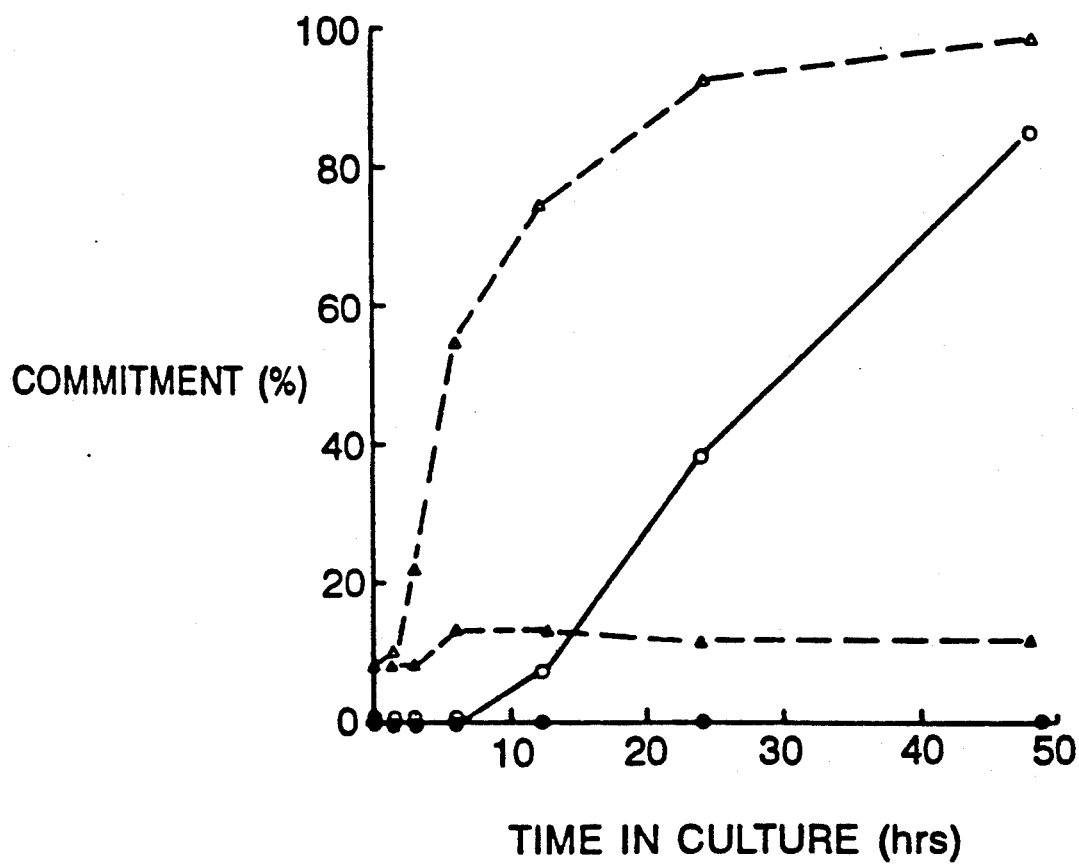

V3.17 cells in culture with HMBA became committed to terminal differentiation and cessation of proliferation at a substantially faster rate than DS19 cells (FIG. 2C). Further, the characteristic latent period of about 12 hrs prior to detectable commitment of cell line DS19 was eliminated for the V3.17 cells in culture with inducer. Whereas DS19 cells display little or no spontaneous commitment, 8 to 14% of the V3.17 cell population are committed in the absence of HMBA.

HMBA Effect on Hemoglobin Accumulation in V3.17 Cells

In the absence of HMBA, hemoglobin accumulation after 98 hrs of culture was less than 0.3 $\mu$g/$10^6$ V3.17 cells and less than 0.1 $\mu$g/$10^6$ DS19 or N23 cells. In culture with HMBA, hemoglobin accumulation is detectable earlier in V3.17 cells (by 24 hrs) than in DS19 or N23 cells (by 48 hrs) and by 98 hrs reaches higher concentrations, that is, 8.1 $\mu$g/$10^6$ cells compared to 4.0 $\mu$g/$10^6$ cells in V3.17 cells and DS19 or N23 cells, respectively.

Sensitivity of V3.17 Cells to HMBA

Figure 3A:
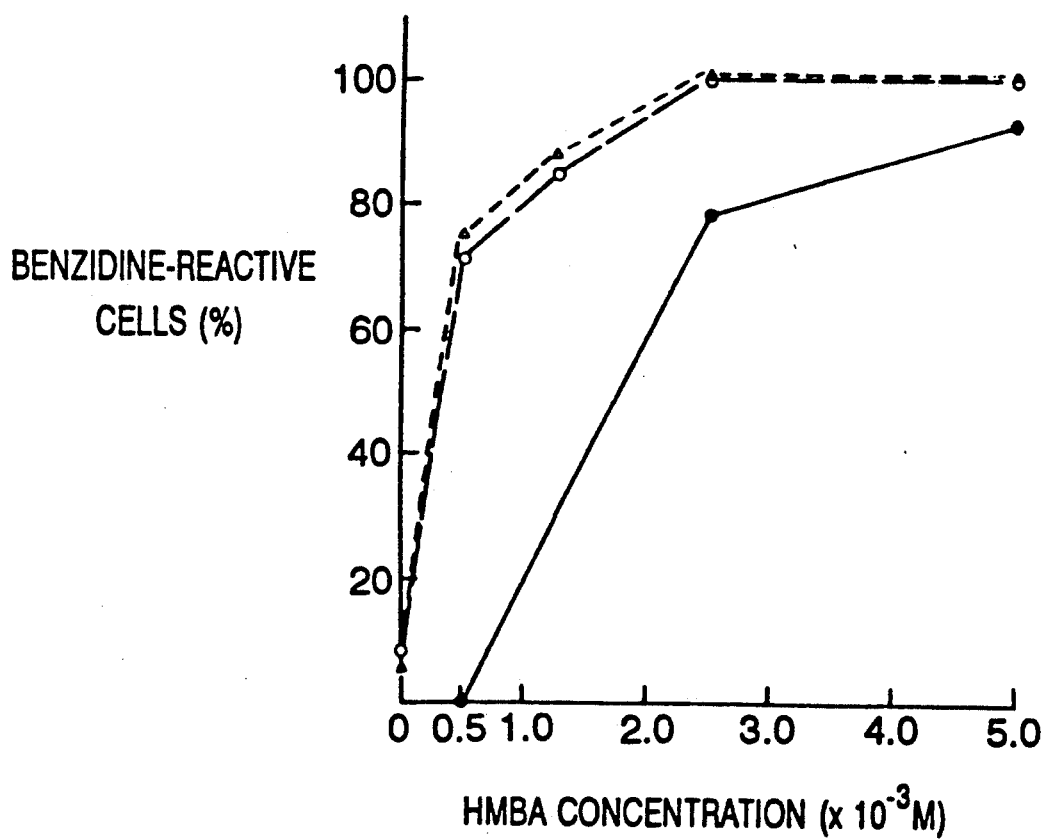
FIGS. 3A and 3B: Effect of HMBA concentration on induction of MEL cell lines DS19 (●); V3.17 cultured without vincristine (○) and V3.17 cultured with vincristine (△). The effect of HMBA on these MEL cell lines was evaluated by determining the proportion of the cells induced to become benzidine-reactive (FIG. 3A) and committed (FIG. 3B).
Figure 3B:
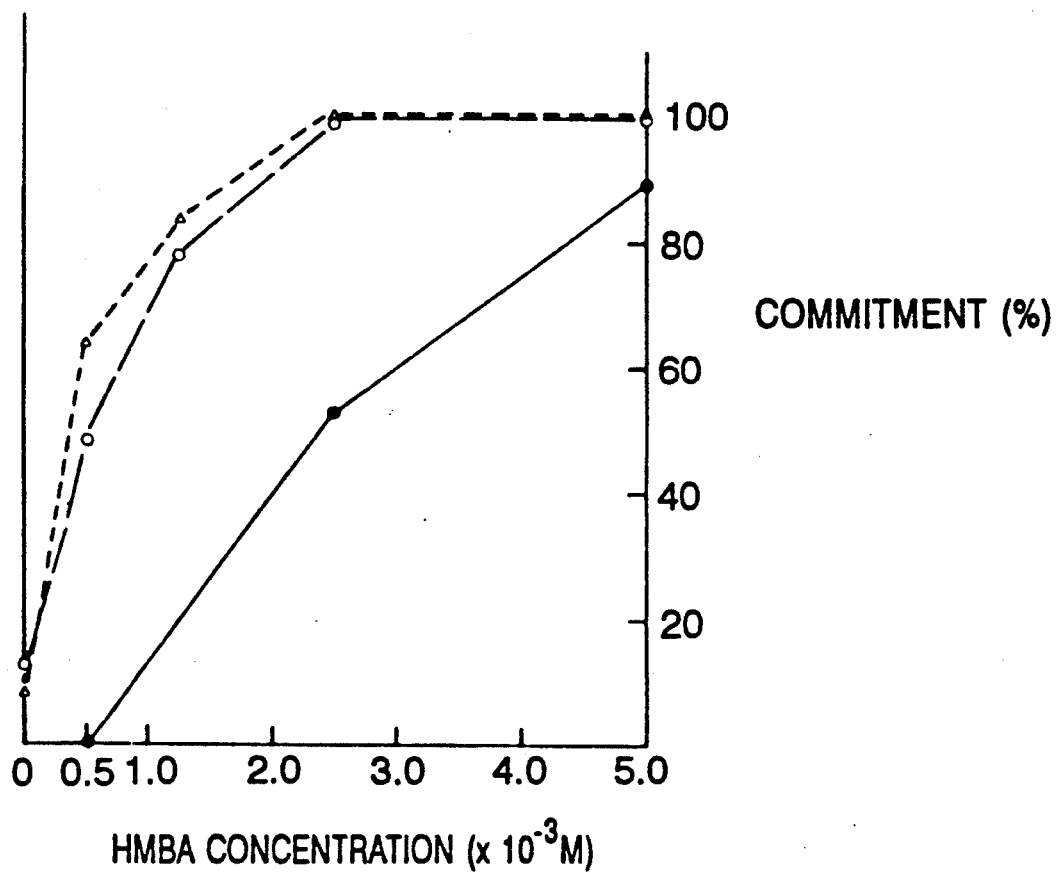

MEL cell lines DS19 and N23 and V3.17 were assayed for sensitivity to induction by HMBA over a range of inducer concentration between $5 \times 10^{-4}$M and $5 \times 10^{-3}$M. The rates of cell growth of DS19, N23 and V3.17 (the last grown in culture without, as well as with 5 ng/ml vincristine) were similar and reached densities of 2.0 to $2.4 \times 10^6$ cells/ml after 5 days. V3.17 cells (cultured without or with 5 ng/ml vincristine) were more sensitive to HMBA-mediated induction than were DS19 or N23 cells, by the dual criteria of proportion of population induced to hemoglobin accumulation (benzidine-reactivity) and commitment to terminal cell differentiation (FIG. 3). For example, $1.25 \times 10^{-3}$M HMBA induced 85 to 88% of V3.17 cells to become benzidine-reactive and 78 to 84% of these cells to become committed, compared to 25% to 30% benzidine-reactive and 15% to 18% committed DS19 cells.

Globin mRNA levels in V3.17 MEL Cells

Figure 4:
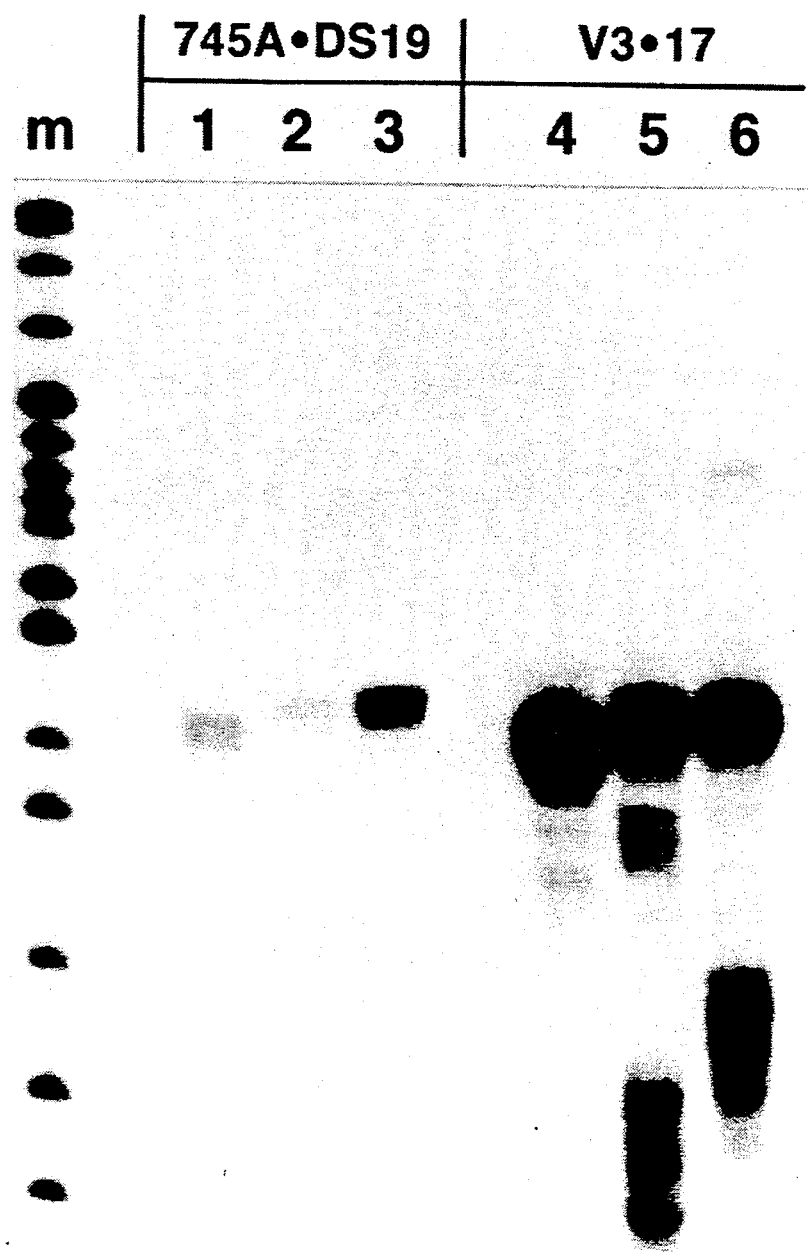
FIG. 4: Analysis of globin mRNAs in uninduced DS19 (vincristine-sensitive) and V3.17 (vincristine-resistant) cells. Total RNA was isolated from log phase growing cells in culture without HMBA; DS19 (lanes 1, 2, and 3) and V3.17 cells (lanes 4, 5, and 6). (lanes 1 and 4) α; (lanes 2 and 5) $\beta^{maj}$; (lanes 3 and 6) $\beta^{min}$. Lane M presents size markers of $^{32}$P-labeled pBR322 DNA cut with MspII.

As previously reported, in uninduced DS19 there are low levels of $\alpha^1$ and $\beta^{min}$ globin gene transcription, and even less $\beta^{maj}$ globin gene transcription (25-27). By comparison, in uninduced V3.17 cells there are approximately 10 fold higher levels of $\alpha^1$, $\beta^{min}$ and $\beta^{maj}$ globin mRNA than in uninduced DS19 (FIG. 4). When cultured with HMBA, V3.17 cells show no increase in accumulated $\alpha^1$, $\beta^{maj}$ or $\beta^{min}$ globin mRNA during the initial 12 hours of culture, by 24 hr an increase in levels of both $\alpha^1$ and $\beta^{maj}$ globin mRNA (but not $\beta^{min}$ globin mRNA) was observed. By 24 hrs in V3.17 in culture with HMBA, $\alpha^1$ globin mRNA had increased almost 6 fold and $\beta^{maj}$ globin mRNA almost 2 fold, relative to uninduced cells. With respect both to the time of onset of HMBA-induced increased accumulation of globin mRNA, and the relative increase in $\alpha^1$ and $\beta^{maj}$ globin mRNA, V3.17 cells are similar to DS19 cells (data not shown).

Effect of Phorbol Ester on V3.17 MEL Cells

Figure 5A:
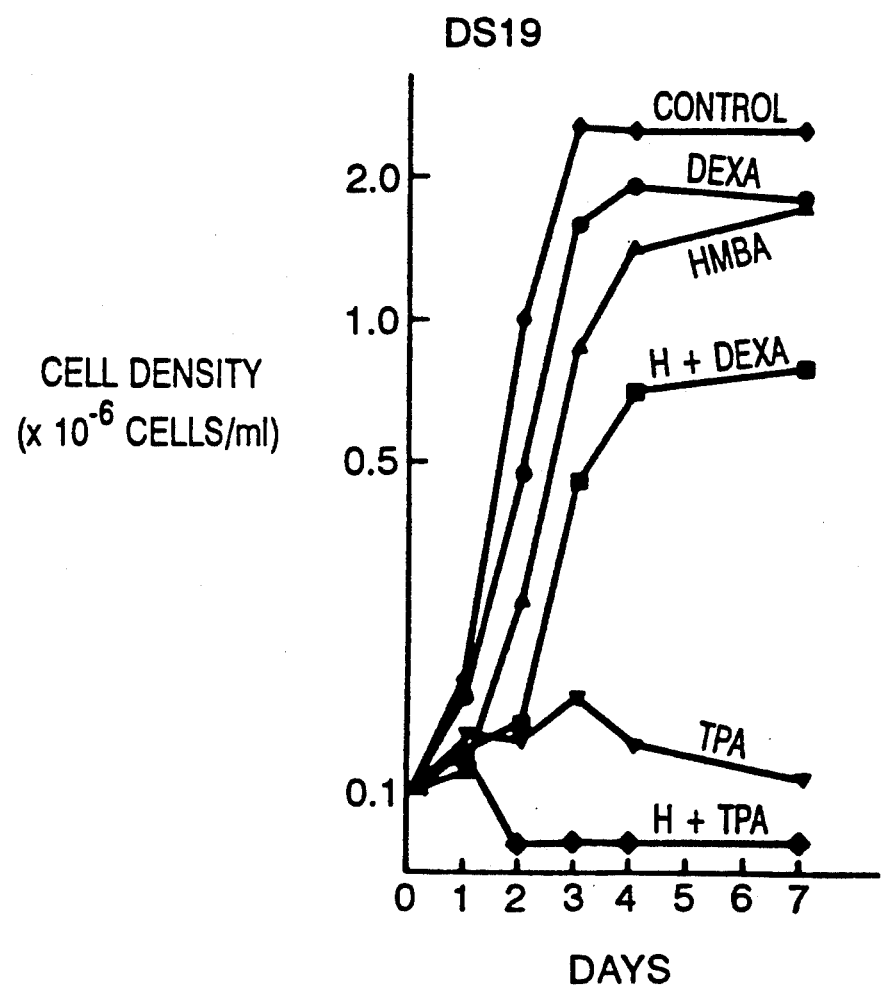
FIGS. 5A and 5B: Effect of TPA and dexamethasone on cell growth of MEL cells DS19 (vincristine-sensitive) and V3.17 (vincristine-resistant). DS19
Figure 5B:
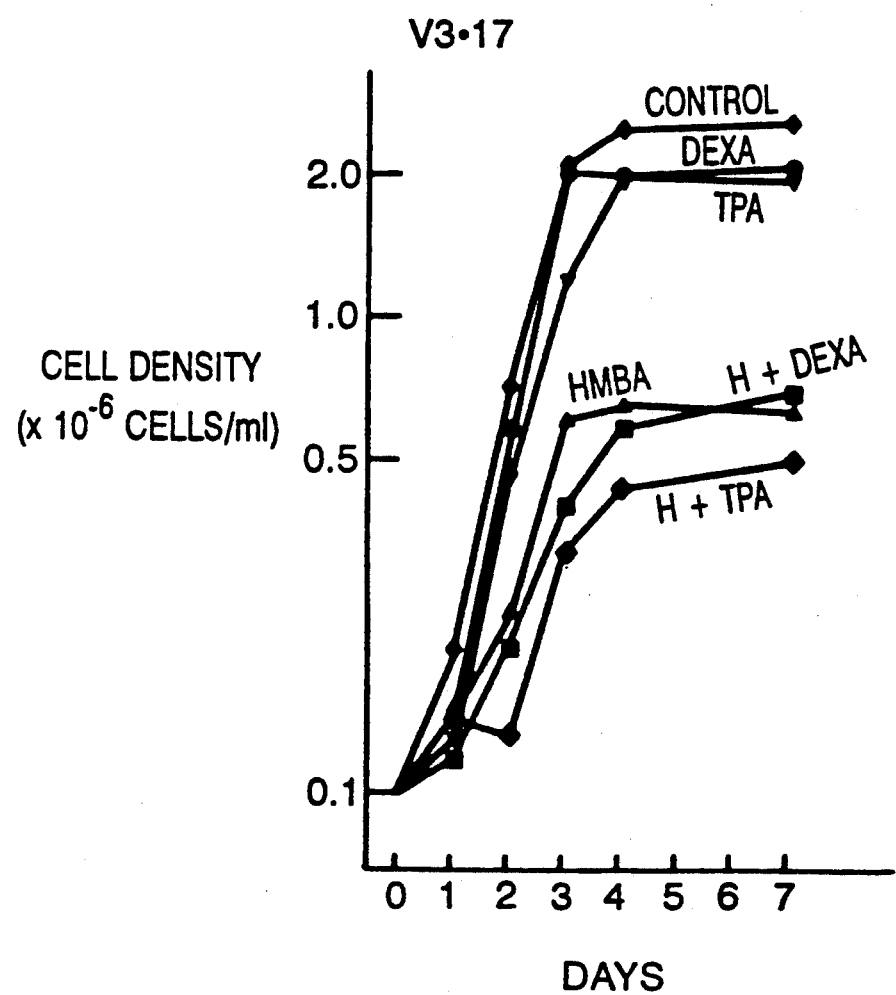

The phorbol ester, TPA, is a potent inhibitor of HMBA-induced commitment of MEL cell line DS19 and it inhibits growth of these cells in concentrations as low as 10 ng/ml TPA (19) (FIG. 5). In contrast, V3.17 cell growth was only mildly inhibited by 10 ng/ml TPA. In culture with both TPA and HMBA, V3.17 cell growth was somewhat more inhibited, but not to the same degree as DS19 cells (FIG. 5). TPA (10 ng/ml) inhibited relatively slightly HMBA-induced V3.17 cell commitment or accumulation of benzidine-reactive cells (Table 1). This is in striking contrast to the complete inhibition by TPA of HMBA-mediated induction of cell lines DS19 (Table 1) or N23 (data not shown).

TABLE 1

Effect of TPA and of Dexamethasone on HMBA-induced commitment and accumulation of benzidine-reactive cells.

| Addition* | DS19 Benzidine Reactive+ (%) | DS19 Commitment# (%) | V3.17** Benzidine Reactive+ (%) | V3.17** Commitment# (%) |
|---|---|---|---|---|
| NONE | 0 | 0 | 7 | 9 |
| HMBA | 90 | 82 | 100 | 97 |
| HMBA + DEXA | 2 | 0 | 85 | 81 |
| HMBA + TPA | 0 | 0 | 80 | 74 |
| DEXA | 0 | 0 | 0 | 4 |
| TPA | 0 | 0 | 2 | 4 |

*Additions as indicated were: HMBA, $5 \times 10^{-3}$M; Dexamethasone (DEXA), $4 \times 10^{-6}$M; TPA, 10 ng/ml.
**V3.17 cultures included 5 ng/ml vincristine as well as the additions indicated.
+Benzidine-reactive cells were scored after six days in culture. Zero means less than or equal to 1.0%.
Commitment was assayed after two days in culture.

Effect of Dexamethasone on V3.17 MEL Cells

Dexamethasone inhibits HMBA-induced expression of terminal differentiation in cell line DS19 (2). V3.17 cells in culture with dexamethasone without or with HMBA displayed growth characteristics similar to DS19 cells cultured under the same conditions (FIG. 5). HMBA-induced V3.17 commitment and accumulation of benzidine-reactive cells was much less inhibited by the steroid than were DS19 cells (Table 1). Furthermore, it was consistently observed that V3.17 cells cultured with TPA or dexamethasone, without inducer, displayed a lower spontaneous level of benzidine-reactive cells (after 5 or 6 days in culture) and a somewhat lower level of spontaneous commitment than V3.17 cells cultured without inhibitor (Table 1).

Protein Kinase C (PKC) Activity in MEL Cells

It has been previously reported that HMBA-mediated MEL cell DS19 differentiation involves a protein kinase C-related mechanism (12). The evidence for this includes the observation that (1) TPA inhibits HMBA-induced MEL cell differentiation and causes depletion of total PKC activity, (2) MEL cells depleted of PKC activity by exposure to TPA are resistant to induction by HMBA, and (3) upon removal of TPA, restoration of sensitivity to HMBA accompanies reaccumulation of PKC activity. The PKC activity in V3.17 was found to be almost two fold higher in the V3.17 cells compared to N23 cells, 7.0 units/$10^6$ cells and 3.9 units/$10^6$ cells, respectively, on the average.

In earlier studies (12), it was found that HMBA induces the formation of a soluble, proteolytically-activated form of PKC that is catalytically active in the absence of $Ca^{2+}$ and phospholipid. The protease inhibitor, leupeptin, blocks formation of this activated form of PKC and inhibits HMBA-induced MEL cell (DS19 or N23) hemoglobin accumulation. Leupeptin (0.1 mM) added to cultures of V3.17 cells inhibited HMBA-mediated induction of benzidine-reactive cells, to approximately the same degree as observed with DS19 or N23 cell lines. This suggests that the V3.17 cells may share with DS19 a common target of leupeptin action which lies on the pathway to induced differentiation.

EXPERIMENTAL DISCUSSION

These studies describe the characteristics of a new variant of MEL cells which was developed as a cell line resistant to vincristine inhibition of cell growth. The concentration of vincristine to which these cells are resistant is 5 ng/ml, a relatively low level of drug resistance since the relative resistance of several established multidrug resistant cell lines is 20 to several hundred fold greater (32). This variant MEL cell line, V3.17, displays remarkable sensitivity to the induction of differentiation by HMBA. V3.17 MEL cells are: (1) induced to commit with little or no latent period characteristic of the induction of DS19 MEL cells; (2) more rapidly induced to accumulate benzidine-reactive cells and commit to terminal cell division than vincristine-sensitive cell lines; (3) responsive to lower concentrations of HMBA, e.g., one tenth the concentration of HMBA optimal for inducing vincristine-sensitive MEL cells will induce well over 50% of V3.17 cells and (4) resistant to both phorbol ester and dexamethasone inhibition of HMBA-induced differentiation.

HMBA induction of the DS19 MEL line is a multistep process (1,17,18) which entails an initial, latent period of approximately 10 to 12 hrs before detectable commitment. In V3.17 cells, the time-dependent process involved in this latent period is essentially eliminated. While this study does not define the mechanism of the altered response to HMBA of V3.17 compared to DS19, the present evidence leads to hypothesize that the lack of the latent period during HMBA-induced differentiation of V3.17 cells may be the result of constitutive expression of a factor which circumvents HMBA-mediated early events in the multistep pathway of induced differentiation.

The initiation of inducer-mediated V3.17 cell commitment with little or no latent period is similar to that seen in DS19 cells cultured with inducer in the presence of a calcium ionophore (9). Certain vincristine-resistant cell lines have been shown to amplify a genomic region which contains a small group of related genes designated mdr (28–31). Several lines of evidence suggest that the mdr protein acts as a drug efflux pump (32). Further, the increased rates of drug removal from multidrug-resistant cells is energy-dependent (33–35) and calcium channel blockers such as verapamil can overcome multidrug resistance in vivo and in vitro (36). Altered ion transport in V3.17 cells could be a factor determining the differences between DS19 and V3.17 cell response to HMBA. Other inducer-mediated events involved in the pathway leading to expression of the terminal erythroid phenotype may be sites of modification in vincristine-resistant MEL cells. There is a transient inhibition of DNA replication, accumulation of single strand DNA breaks and prolongation of $G_1$ during HMBA induction of DS19 cells (37,38). Inhibition of DNA replication is associated with accumulation of a factor, probably a protein, which acts synergistically with a second factor, also induced by HMBA, to cause commitment (39-41). The latter activity is short-lived and inhibited by TPA. It will be interesting to test whether this TPA-sensitive factor is present in V3.17 cells.

Vincristine can prevent tubulin polymerization leading to microtubules formation and, thus, exert an antimitotic effect (42). In V3.17 MEL cells a change in tubulin structure may account for the resistance of these cells to vincristine and an alteration in cell cycle progression which could be associated with the altered response of V3.17 cells to HMBA.

It has been previously reported that the tumor promotor, TPA, and the steroid, dexamethasone, are potent inhibitors of HMBA-induced DS19 cell differentiation (2,19). The evidence from these studies indicated that HMBA, in the presence of TPA or dexamethasone, initiates changes which prepare MEL cells for commitment to terminal cell division and globin gene expression, since removing the inhibitors is associated with very rapid commitment, without additional latent period (2). V3.17 cells, which are not as sensitive to TPA or dexamethasone, may have established certain charges which are inducer-mediated in DS19 cells and are the target of TPA and dexamethasone block to terminal differentiation.

It has been recently found that PKC activity plays a role in HMBA-induced modulation of globin gene expression (12). PKC activity can be increased several fold in certain drug-resistant tumor cell lines (43-44). An almost two-fold greater PKC activity in vincristine-resistant MEL cells was found when compared to vincristine-sensitive cells. The increased PKC activity in vincristine-resistant cells does not abolish the capacity of leupeptin, a protease inhibitor which blocks the conversion of PKC to the soluble, $Ca^{2+}$ and phospholipid independent but catalytically active form of the enzyme, to inhibit HMBA-mediated differentiation. The effect of leupeptin in blocking HMBA-induced hemoglobin accumulation was similar with V3.17 and DS19 or N23 cells. This provides further evidence of a role for proteolysis in MEL cell-induced differentiation and the possible involvement of a soluble, $Ca^{2+}$ and phospholipid-independent form of the kinase.

The V3.17 MEL cell line provides a tool to further dissect the steps involved in HMBA-mediated MEL cell terminal erythroid differentiation.

REFERENCES

1. Marks, P. A., Sheffery, M. and Rifkind, R. A. (1987) Cancer Res. 47, 659–666.
2. Chen, Z., Banks, J., Rifkind, R. A. and Marks, P. A. (1982) Proc. Natl. Acad. Sci. (USA) 79, 471–475.
3. Friend, C., Scher, W., Holland, J., and Sato, T. (1971) Proc. Natl. Acad. Sci. (USA) 68, 378–382.
4. Reuben, R. C., Wife, R. L., Breslow, R., Rifkind, R. A. and Marks, P. A. (1976) Proc. Natl. Acad. Sci. (USA) 73., 862–866 (1976).
5. Gusella, J. F., Geller, R., Clarke, B., Weeks, V. and Housman, D. (1976) Cell 9, 221–229.
6. Fibach, E., Reuben, R. C., Rifkind, R. A. and Marks, P. A. (1977) Cancer Res. 37, 440–444.
7. Mager, D. and Bernstein, A. (1978) J. Supermolec. Structure 8, 431–438.
8. Cantley, L., Bernstein, A., Hunt, D. M., Crichley, V. and Mak, T. W. (1976) Cell 9, 375–381.
9. Bridges, K., Levenson, R., Housman, D. and Cantley, L. (1981) J. Cell Biol. 90, 542–544.
10. Gazitt, Y., Deitch, A. D., Marks, P. A. and Rifkind, R. A. (1978) Exp. Cell Res. 117, 413–420.
11. Gazitt, Y., Reuben, R. C., Deitch, A. D., Marks, P. A. and Rifkind, R. A. (1978) Cancer Res. 38, 3779–3783.
12. Melloni, E., pontremoli, S., Michetti, M., Sacco, O., Cakiroglu, A. G., Jackson, J. F., Rifkind, R. A., and Marks, P. A. (1987) Proc. Natl. Acad. Sci. 84, 5282–5286.
13. Lachman, H. M. and Skoultchi, A. I. (1984) Nature 310, 592–594.
14. Kirsch, I. R., Bertness, V., Silver, J. and Hollis, G. (1985) Oncogene regulation during erythroid differentiation. In: *Leukemia: Recent Advances in Biology and Treatment*, 91-98, Alan R. Liss, Inc., N.Y.
15. Ramsay, R. G., Ikeda, K., Rifkind, R. A., and Marks, P. A. (1986) Proc. Natl. Acad. Sci. (USA) 83, 6849–6853.
16. Todokoro, K. and Ikawa, Y. (1986) Biochem. Biophys. Res. Comm. 135, 1112–1118.
17. Marks, P. A. and Rifkind, R. A. (1978) Ann. Rev. Biochem. 47, 419–448.
18. Tsiftsoglou, A. S. and Robinson, S. H. (1985) Int. J. Cell Cloning 3. 349–366.
19. Yamasaki, H., Fibach, E., Nudel, U., Weinstein, I. B., Rifkind, R. A. and Marks, P. A. ( 1977 ) Proc. Natl. Acad. Sci. (1977) 74, 3451–3455.
20. Ohta, Y., Tanaka, M., Terada, M., Miller, O. J., Bank, A., Marks, P. A. and Rifkind, R. A. (1976) Proc. Natl. Acad. Sci. USA 73, 1232–1236.
21. Ullrich, A., Shine, J., Chirguin, J., Pictect, R., Tischer, E., Rutter, W. J. and Goodman, H. M. (1977) Science 196, 1313–1318.
22. Glisin, V., Crkvenjakov, R. & Byus, C. (1974) Biochemistry 13, 2633–2637.
23. Weich, N., Marks, P. A. & Rifkind, R. A. (1988) Biochem. Biophys. Res. Comm. (In Press).
24. Melton, D. A., Krieg, P. A., Rebagliati, M. R., Maniatis, T., Zinn, K. & Green, M. R. (1984) Nucleic Acids Research 12, 7035-7056.
25. Nudel, U., Salmon, J., Fibach, E., Terada, M., Rifkind, R. A., Marks, P. A. and Bank, A. (1977) Cell 12, 463–469.
26. Curtis, P., Finnigan, A. C. and Rovera, G. (1980) J. Biol. Chem. 255, 8971–8964.
27. Sheffery, M., Marks, P. A. and Rifkind, R. A. (1984) J. Mol. Biol. 172, 417–436.
28. Gros, P., Neriah, Y. B., Croop, J. M. and Housman, D. E. (1986) Nature 323: 728–730.
29. Roninson, I. B., Chin, J. E., Choi, K., Gros, P., Housman, D. E., Fojo, A., Shen, D. -W., Gottesman, M. M. and Pastan, I. (1986) Proc. Natl. Acad. Sci. USA 83, 4538–4542.
30. Van der Blick, A. M., Van der Velde-Koerts, T., Ling, V. and Borst, P. (1986) Mol. & Cell. Biol. 6, 1671–1678.
31. Croop, J. M., Guild, B. C., Gros, P. and Housman, D. E. (1987) Cancer Res. 47, 5982–5988.

32. Beidler, J. L., Meyers, M. B., Spengler, B. A. (1988) Bristol-Myers Cancer Symposia 9. (In Press)
33. Dano, K. (1983) Biochim. Biophys. Acta 323, 446–483.
34. Skovsgaard, T. (1978) Cancer Res. 38, 4722–4727.
35. Fojo, A., Akiyama, S., Gottesman, M. and Pastan, I. (1985) Cancer Res. 45, 3002–3007.
36. Tsuruo, T., Lida, H., Tsukagoshi, S. and Sakurai, Y. (1982) Cancer Res. 42, 4730–4733.
37. Terada, M., Nudel, U., Fibach, E., Rifkind, R. A. and Marks, P. A. (1978) Cancer Res. 38, 835–840.
38. Terada, M., Fried, J., Nudel, U., Fibach, E., Rifkind, R. A. and Marks, P. A. (1977) Proc. Natl. Acad. Sci. USA 74, 248–252.
39. Kaneko, T., Nomura, S., Oishi, M. (1984) Cancer Res. 44, 1756–1760.
40. Nomura, S., Yamagoe, S., Kamiya, T., Oishi, M. (1986) Cell 44, 663–669.
41. Watanabe, T., Nomura, S., Oishi, M. (1985) Exp. Cell. Res. 159, 224–234.
42. Schiff, P.B. and Horwitz, S. B. (1981) Bristol-Myers Cancer Symposia 2, 483–507.
43. Fine, R. L., Patel, J., Hamilton, T. C., Cowan, K., Curt, G. A., Friedman, M. A. and Chabner, B. A. (1986) Proc. Am. Assoc. Ca. Res. (abst.) 27, 2.Aquino, A.,
44. Hartman, K. D., Grant, S. and Glazer, R. I. (1987) Proc. Am. Ca. Res. (abst.) 28, 291.

What is claimed is:

1. A method of treating a patient having a tumor sensitive to treatment with the compound below and characterized by proliferation of neoplastic cells which comprises administering to the patient an amount of vincristine effective to render the cells resistant to vincristine and subsequently administering to the patient an amount of a compound effective to selectively induce terminal differentiation of such neoplastic cells and thereby inhibit their proliferation, the compound having the structure:

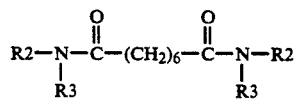

wherein R2 and R3 are independently the same or different and are a hydrogen atom, or a lower alkyl, alkenyl, or alkynyl group.

2. A method of treating a patient having a tumor sensitive to treatment with the compound below characterized by proliferation of neoplastic cells which comprises administering to the patient an amount of vincristine effective to render the cells resistant to vincristine and subsequently administering to the patient an amount of a compound effective to selectively induce terminal differentiation of such neoplastic cells and thereby inhibit their proliferation, the compound having the structure:

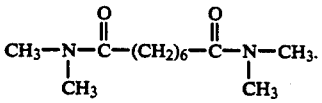

3. The method of claim 1, wherein the cells are rendered resistant to vincristine at a concentration of about 5 mg/ml.

4. The method of claim 1, wherein the antitumor agent is administered so that the concentration of the antitumor agent in the patient's plasma is about 5 mg/ml.

5. The method of claim 1, wherein the administering of the compound is effected once continuously for at least 5 days.

6. The method of claim 1, wherein the administering of the compound is effected at intervals of 25–35 days and continuously for at least 5 days during each such interval.

7. The method of claim 1, wherein the amount of the compound is less than an amount which causes the concentration of the compound in the plasma of the patient to equal about 1.5 mM.

8. The method of claim 1, wherein the amount of the compound is from about 10 gm/m$^2$/day to about 30 gm/m$^2$/day.

9. The method of claim 1, wherein the administering of the compound and the antitumor agent is effected intravenously.

10. The method of claim 1, wherein the tumor is a lung cancer, acute lymphoid myeloma, bladder melanoma, renal carcinoma, breast carcinoma or colorectal carcinoma.

11. The method of claim 2, wherein the cells are rendered resistant to vincristine at a concentration of about 5 mg/ml.

12. The method of claim 2, wherein the antitumor agent is administered so that the concentration of the antitumor agent in the patient's plasma is about 5 mg/ml.

13. The method of claim 2, wherein the administering of the compound is effected once continuously for at least 5 days.

14. The method of claim 2, wherein the administering of the compound is effected at intervals of 25–35 days and continuously for at least 5 days during each such interval.

15. The method of claim 2, wherein the amount of the compound is less than an amount which causes the concentration of the compound in the plasma of the patient to equal about 1.5 mM.

16. The method of claim 2, wherein the amount of the compound is from about 10 gm/m$^2$/day to about 30 gm/m$^2$/day.

17. The method of claim 2, wherein the administering of the compound and the antitumor agent is effected intravenously.

18. The method of claim 2, wherein the tumor is a lung cancer, acute lymphoid myeloma, bladder melanoma, renal carcinoma, breast carcinoma or colorectal carcinoma.

* * * * *